(12) United States Patent
Meyer et al.

(10) Patent No.: US 6,468,444 B1
(45) Date of Patent: Oct. 22, 2002

(54) CHIRAL COMPOUNDS AND THEIR USE AS CHIRAL DOPANTS FOR PRODUCING CHOLESTERIC LIQUID CRYSTAL COMPOSITIONS

(75) Inventors: Frank Meyer, Heidelberg; Peter Schuhmacher, Mannheim; Frank Prechtl, Frankfurt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/531,468

(22) Filed: Mar. 20, 2000

(30) Foreign Application Priority Data

Mar. 25, 1999 (DE) .......................... 199 13 604

(51) Int. Cl.$^7$ .................. C09K 19/36; C09K 19/32; C09K 19/58; A61K 7/00; C07D 493/04; C07D 307/78; C07D 307/93

(52) U.S. Cl. ............... 252/299.7; 252/299.62; 424/59; 424/60; 424/401; 514/772; 514/772.3; 549/464; 549/465; 549/473

(58) Field of Search .............. 252/299.01, 299.62, 252/299.5, 299.61; 106/287.35, 287.21; 514/772, 772.3; 424/59, 60, 400, 401; 549/50, 464, 465, 473

(56) References Cited

U.S. PATENT DOCUMENTS

| | | | |
|---|---|---|---|
| 5,744,057 A | 4/1998 | Meyer | |
| 5,780,629 A | 7/1998 | Etzbach | 544/296 |
| 5,788,880 A | 8/1998 | Schierlinger | 252/299.61 |
| 5,827,449 A | 10/1998 | Hanelt | |
| 5,833,880 A | 11/1998 | Siemensmeyer | 252/299.64 |
| 5,851,277 A | 12/1998 | Mueller-Rees | |
| 5,886,242 A | 3/1999 | Etzbach | 585/25 |
| 6,060,042 A | 5/2000 | Schuhmacher et al. | 424/60 |
| 6,159,454 A * | 12/2000 | Schuhmacher et al. | 429/59 |
| 6,217,792 B1 * | 4/2001 | Parri et al. | 262/299.61 |

FOREIGN PATENT DOCUMENTS

| | | |
|---|---|---|
| DE | 43 42 280 | 6/1995 |
| DE | 19532408 | 3/1997 |
| DE | 19541820 | 5/1997 |
| DE | 19629761 | 6/1997 |
| DE | 19611101 | 9/1997 |
| DE | 19619460 | 11/1997 |
| DE | 19738369 | 3/1999 |
| EP | 750 029 | 12/1996 |
| EP | 962 222 A2 | 12/1999 |
| EP | 998 900 A1 | 5/2000 |
| GB | 2 314 839 | 1/1998 |
| WO | 95/16007 | 6/1995 |
| WO | WO 97/00600 | 1/1997 |
| WO | 98/00428 | 1/1998 |

OTHER PUBLICATIONS

Makromol. Chem 179, 829–832 (1978) Finkelmann et al.

\* cited by examiner

Primary Examiner—Shean C. Wu
(74) Attorney, Agent, or Firm—Keil & Weinkauf

(57) ABSTRACT

Chiral dopants of the formula I $$Z^1-Y^1-(A^1)_m-Y^2-M-Y^3-X-Y^4-(A^2)_n-Y^5-Z^2 \quad I$$

in which the variables have, independently of one another, the following meanings:

$A^1$ and $A^2$
  a spacer with a chain length of 1 to 30 carbon atoms;

$Y^1$ to $Y^5$
  a chemical bond, —O—, —S—, —C(=O)—, —C(=O)—O—, —O—C(=O)—, —CH=CH—C(=O)—O—, —O—C(=O)—O—, —C(=O)—N(R)— or —(R)N—C(=O)—, —CH$_2$—O—, —O—CH$_2$—, —CH=N—, —N=CH— or —N=N—;

M a mesogenic group;

R hydrogen, $C_1$–$C_4$-alkyl;

$Z^1$ and $Z^2$
  hydrogen, $C_1$–$C_4$-alkyl, a polymerizable group or a radical having a polymerizable group;

x a dianhydrohexitol residue selected from the group consisting of dianhydrosorbitol, dianhydromannitol and dianhydroiditol;

m/n 0 or 1, where the radicals $Z^1$, $Z^2$, $Y^1$ to $Y^5$, $A^1$ and $A^2$ can be identical or different, and at least one $Z^1$ or $Z^2$ radical is a polymerizable group or a radical having a polymerizable group, and their use as chiral dopants for producing cholesteric liquid crystal compositions which can be employed as UV filters in cosmetic and pharmaceutical preparations.

11 Claims, No Drawings

CHIRAL COMPOUNDS AND THEIR USE AS CHIRAL DOPANTS FOR PRODUCING CHOLESTERIC LIQUID CRYSTAL COMPOSITIONS

FIELD OF THE INVENTION

The invention relates to chiral compounds and to the use thereof as chiral dopants for producing cholesteric liquid crystal compositions which can be employed as photostable UV filters in cosmetic and pharmaceutical preparations for protecting the human epidermis or human hair from UV radiation, specifically in the range from 280 to 450 nm.

BACKGROUND OF THE INVENTION

Cholesteric liquid crystals (CLCs) reflect circularly polarized electromagnetic radiation in a wavelength range dependent on the helical structure of the CLC. The central wavelength of the reflection band is determined by the pitch p of the helical structure, and the width of the band by the optical anisotropy of the mesogens. The central wavelength of the reflection band, which is referred to hereinafter as the reflection wavelength, depends on the angle of view. The direction of rotation of the reflected light corresponds to the direction of rotation of the cholesteric helix.

Cholesteric liquid crystal mixtures usually contain one or more optically active components to induce a chiral structure. For example, cholesteric liquid crystal mixtures may consist of a nematic base material and one or more optically active dopants. The latter generate in the nematic either a right or left-handed twist which determines the direction of rotation of the reflected circularly polarized light.

Numerous compounds are known as chiral dopants for liquid crystal phases (e.g. from DE-A 43 42 280, DE-A 195 41 820 and DE-A 196 11 101, and from GB-A-2 314 839 and WO 98/00428).

Frequently suitable for left-helical materials are cholesterol compounds which, apart from the chirality, also introduce sufficient mesogenic properties to generate a stable mesophase. Compounds of this type are described, for example, by H. Finkelmann, H. Ringsdorf et al., in Makromol. Chem. 179, 40 829–832 (1978). However, these compounds have the disadvantage of a complicated synthesis and a high cost of preparation.

SUMMARY OF THE INVENTION

It is an object of the present invention to provide novel chiral compounds which are suitable for producing cholesteric liquid crystal compositions that do not have the above-mentioned disadvantages.

We have found that this object is achieved by chiral dopants of the formula I $$Z^1-Y^1-(A^1)_m-Y^2-M-Y^3-X-Y^4-(A^2)_n-Y^5-Z^2 \quad \text{I}$$

in which the variables have, independently of one another, the following meanings:

A$^1$ and A$^2$
  a spacer with a chain length of 1 to 30 C atoms;
Y$^1$ to Y$^5$
  a chemical bond, —O—, —S—, —C(=O)—, —C(=O)—O—, —O—C(=O)—, —CH=CH—C(=O)—O—, —O—C(=O)—O—, —C(=O)—N(R)— or —(R)N—C(=O)—, —CH$_2$—O—, —O—CH$_2$—, —CH=N—, —N=CH— or —N=N—;

M a mesogenic group;
R hydrogen, C$_1$–C$_4$-alkyl;
Z$^1$ and Z$^2$
  hydrogen, C$_1$–C$_4$-alkyl, a polymerizable group or a radical having a polymerizable group;
X a dianhydrohexitol residue selected from the group consisting of dianhydrosorbitol, dianhydromannitol and dianhydroiditol;
m 0 or 1;
n 0 or 1,
where the radicals Z$^1$, Z$^2$, Y$^1$ to Y$^5$, A$^1$ and A$^2$ can be identical or different, and at least one Z$^1$ or Z$^2$ radical is a polymerizable group or a radical comprising a polymerizable group.

Suitable spacers A$^1$ and A$^2$ are all groups known for this purpose. The spacers usually contain 1 to 30, preferably 1 to 12, particularly preferably 1 to 6, C atoms and consist of predominantly linear aliphatic groups. They may be interrupted in the chain, for example, by nonadjacent oxygen or sulfur atoms or imino or alkylimino groups such as methylimino groups.

Substituents suitable for the spacer chain are moreover fluorine, chlorine, bromine, cyano, methyl and ethyl.

Examples of representative spacers are:

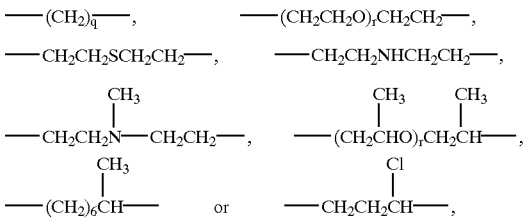

where r is 1 to 3 and q is 1 to 12.

Preferred spacers are ethylene, propylene, n-butylene, n-pentylene and n-hexylene.

In a preferred embodiment, however, it is also possible to link the dianhydrohexitol residue X without spacer directly to the radical Z$^2$. In this case, n is 0 and Y$^4$ or Y$^5$ is a chemical bond.

It is also possible to link the mesogenic radical M without spacer directly to the radical Z$^1$. In this case, m is 0 and Y$^1$ or Y$^2$ is a chemical bond.

All known mesogenic groups can be used as M radicals.
Particularly suitable mesogenic groups are those of the formula

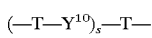

in which the variables have the following meanings:

T identical or different divalent saturated or unsaturated iso- or heterocyclic radicals,
Y$^{10}$ groups of the definition for Y$^1$ to Y$^5$,
s 0, 1, 2 or 3,
where in the case where s>0, both the T radicals and the Y$^{10}$ groups can each be identical to or different from one another.

It is preferred for s to be 1 or 2.
The T radicals may also be ring systems substituted by fluorine, chlorine, bromine, cyano, hydroxyl or nitro. Preferred T radicals are:

Examples of preferred mesogenic groups M are:

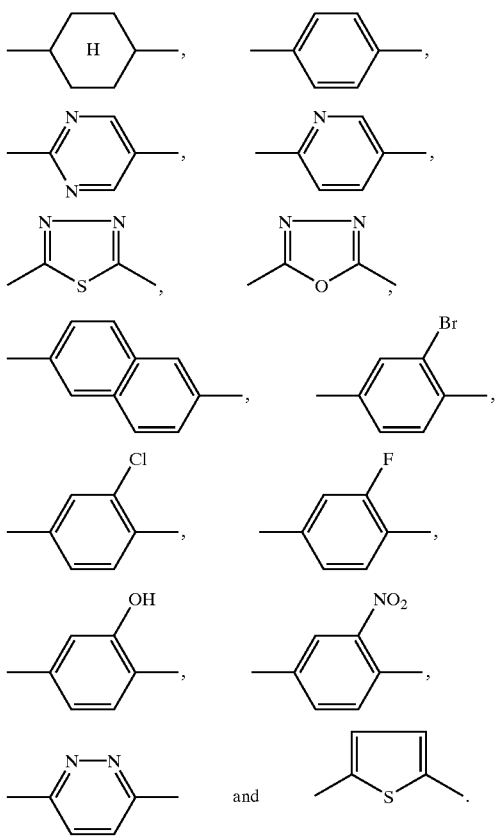
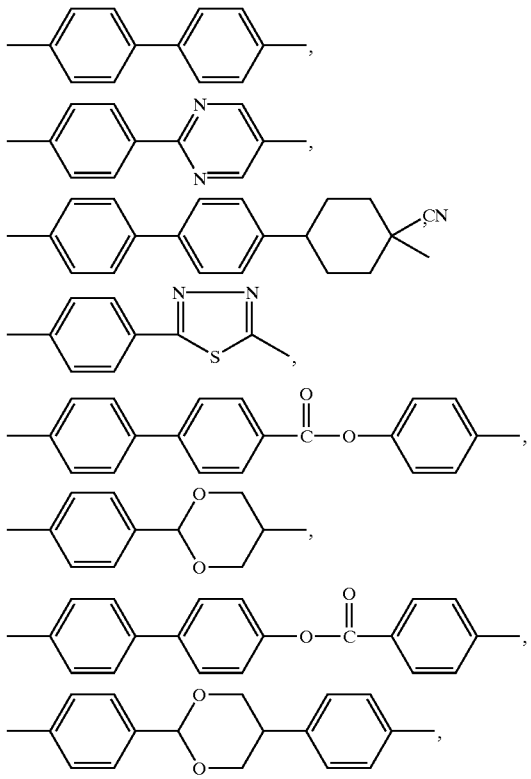

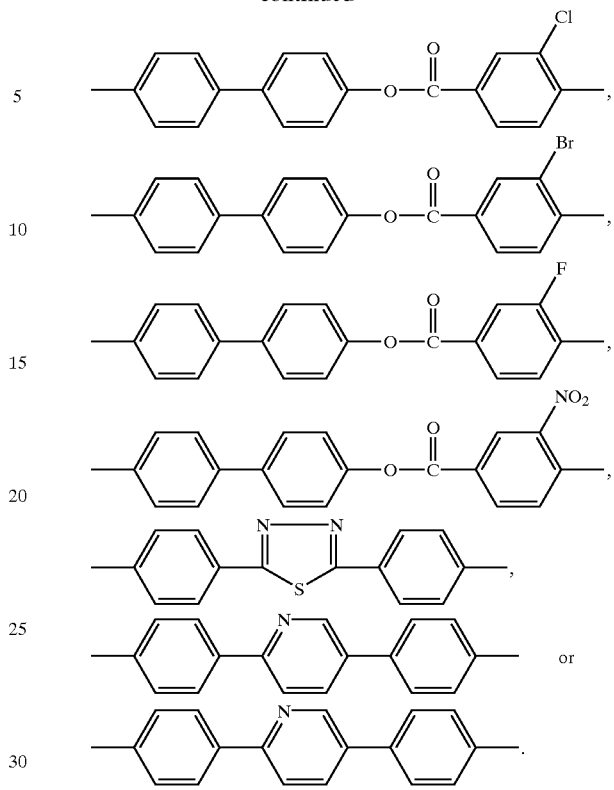

Particularly preferred mesogenic groups M are those of the following formulae

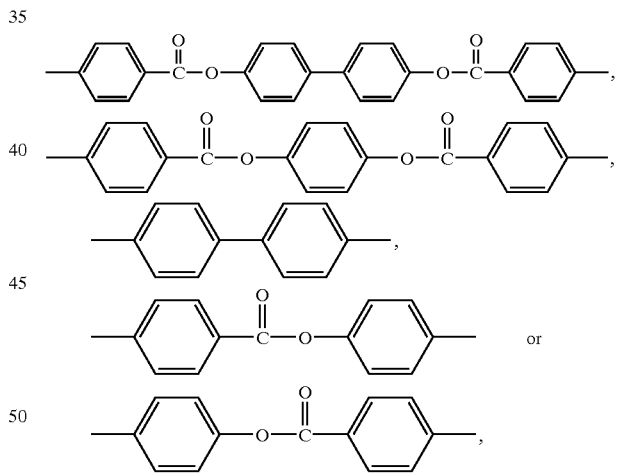

where each aromatic ring may have up to three identical or different substituents from the following group:

hydrogen, $C_1$–$C_{20}$-alkyl, $C_1$–$C_{20}$-alkoxy, $C_1$–$C_{20}$-alkoxycarbonyl, $C_1$–$C_{20}$-monoalkylaminocarbonyl, $C_1$–$C_{20}$-alkylcarbonyl, $C_1$–$C_{20}$-alkylcarbonyloxy, $C_1$–$C_{20}$-alkylcarbonylamino, formyl, halogen, cyano, hydroxyl or nitro.

Preferred substituents for the aromatic rings are, besides fluorine, chlorine, bromine, cyano, formyl and hydroxyl, especially short-chain aliphatic radicals such as methyl, ethyl, n-propyl, i-propyl, n-butyl, i-butyl, sec-butyl, tert-butyl, and alkoxy, alkoxycarbonyl, alkylcarbonyl, alkylcarbonyloxy, alkylcarbonylamino and monoalkylaminocarbonyl radicals which contain these alkyl groups.

The outer benzene rings of the particularly preferred M groups preferably have the following substitution patterns:

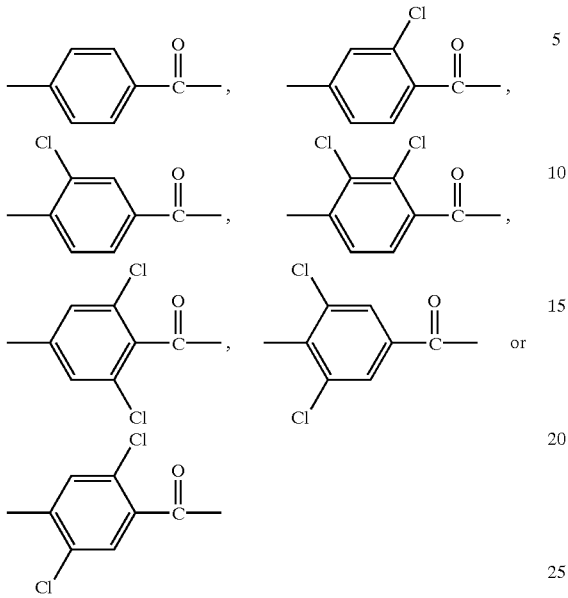

or they are substituted analogously with F, Br, CH$_3$, OCH$_3$, CHO, COCH$_3$, OCOCH$_3$ or CN in place of Cl, it also being possible for mixed substituents to be present. Mention should also be made of the structures

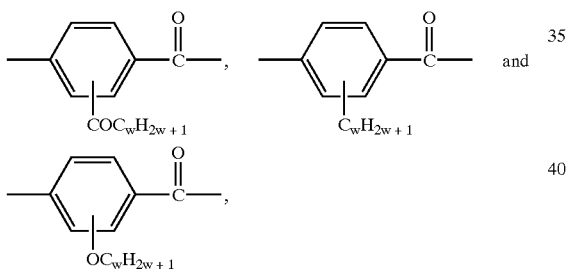

in which w is 2 to 20, preferably 8 to 15.

The preferred substitution patterns of the middle benzene ring of the particularly preferred M groups are

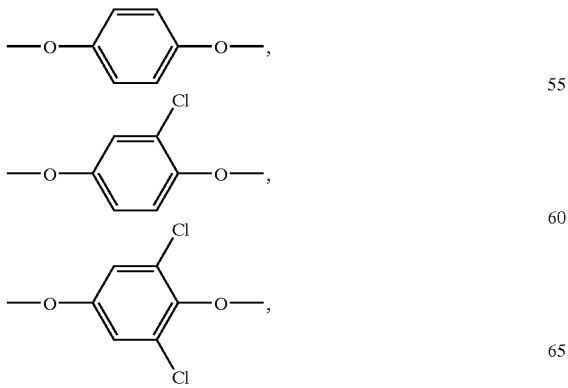

-continued

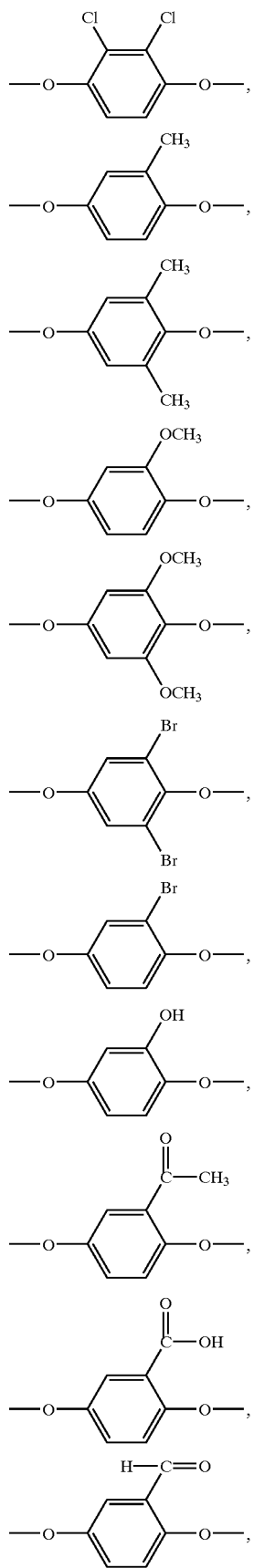

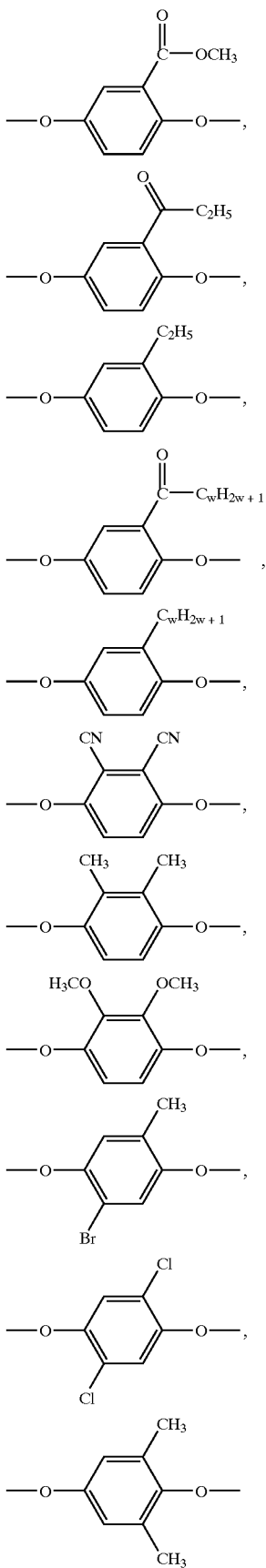

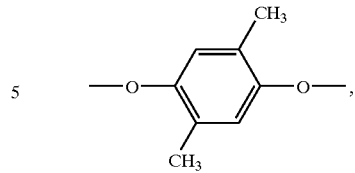

Alkyl radicals which may be mentioned for R and for $Z^1$ and $Z^2$ are branched or unbranched $C_1$–$C_4$-alkyl chains, preferably methyl, ethyl, n-propyl, 1-methylethyl, n-butyl, 1-methylpropyl-, 2-methylpropyl or 1,1-dimethylethyl.

Preferred $Z^1$ and $Z^2$ radicals are:

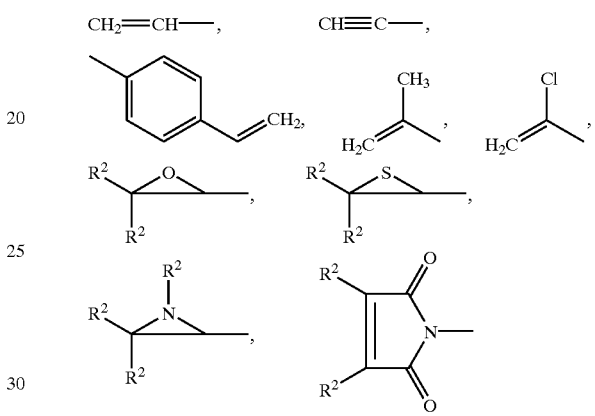

—N=C=O, —N=C=S, —O—C≡N, —COOH, —OH or $NH_2$ where the $R^2$ radicals may be identical or different and are hydrogen or $C_1$–$C_4$-alkyl such as methyl, ethyl, n-propyl, iso-propyl, n-butyl, iso-butyl, sec-butyl or tert-butyl. Of the reactive polymerizable groups, the cyanates are capable of spontaneous trimerization to cyanurates and are therefore preferred. The other groups mentioned require other compounds with complementary reactive groups for the polymerization. Thus, for example, isocyanates can polymerize with alcohols to form urethanes and with amines to form urea derivatives. Analogous statements apply to thuiranes and aziridines. Carboxyl groups can be condensed to form polyesters and polyamides. The maleimido group is particularly suitable for free-radical copolymerization with olefinic compounds such as styrene. The complementary reactive groups may moreover either be present in a second compound according to the invention, which is mixed with the first, or be incorporated into the polymeric network by auxiliary compounds containing 2 or more of these complementary groups.

Particularly preferred $Z^1$—$Y^1$ and $Y^5$—$Z^2$ groups are acrylate and methacrylate.

$Y^1$—$Y^5$ may have the abovementioned meanings, with a chemical bond being intended to mean a single covalent bond.

Suitable dianhydrohexitol residues are selected from the group consisting of dianhydrosorbitol, dianhydromannitol and dianhydroiditol. Dianhydrosorbitol and dianhydromannitol residues are preferred, and dianhydromannitol is particularly preferred.

Particularly preferred chiral dopants are those containing dianhydromannitol and having the formula Ia

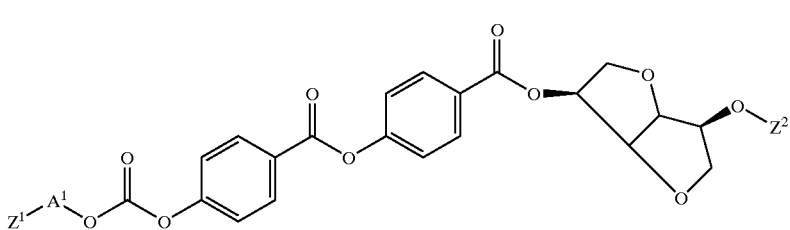

Ia in which the variables have, independently of one another, the following meanings:

$A^1$
a spacer with a chain length of 1 to 6 C atoms;

$Z^1$ and $Z^2$
a polymerizable group or a radical having a polymerizable group, where the definition of the variables $A^1$, and $Z^1$ and $Z^2$ corresponds in the general and in the preferred embodiment to the explanation given above.

The abovementioned compounds are prepared in a manner known per se by the processes described in DE-A-195 32 408, DE-A-44 08 171, EP-A-0 750 029 and WO 95/16007. Reference may be made to these publications for further details.

The chiral compounds according to the invention of the formula I are suitable inter alia as chiral dopants for producing cholesteric liquid crystal compositions, in particular cholesteric liquid crystals with a left-hand twist.

The invention therefore also relates to cholesteric liquid crystal compositions comprising a) at least one chiral liquid crystal polymerizable monomer of the formula I $$Z^1-Y^1-(A^1)_m-Y^2-M-Y^3-X-Y^4-(A^2)_n-Y^5-Z^2 \qquad I$$

in which the variables have, independently of one another, the following meanings:

$A^1$ and $A^2$
a spacer with a chain length of 1 to 30 C atoms;

$Y^1$ to $Y^5$
a chemical bond, —O—, —S—, —C(=O)—, —C(=O)—O—, —O—C(=O)—, —CH=CH—C(=O)—O—, —O—C(=O)—O—, —C(=O)—N(R)— or —(R)N—C(=O)—, —CH$_2$—O—, —O—CH$_2$—, —CH=N—, —N=CH— or —N=N—;

M a mesogenic group;

R hydrogen, C$_1$–C$_4$-alkyl;

$Z^1$ and $Z^2$
hydrogen, C$_1$–C$_4$-alkyl, a polymerizable group or a radical having a polymerizable group;

X a dianhydrohexitol residue selected from the group consisting of dianhydrosorbitol, dianhydromannitol and dianhydroiditol;

m 0 or 1;

n 0 or 1 where the radicals $Z^1$, $Z^2$, $Y^1$ to $Y^5$, $A^1$ and $A^2$ can be identical or different, and at least one $Z^1$ or $Z^2$ radical is a polymerizable group or a radical comprising a polymerizable group, with which monomer it is possible to obtain a cholesteric liquid crystal phase with a pitch of less than 450 nm or b) a mixture of b$_1$) at least one achiral liquid crystal polymerizable monomer of the formula II $$Z^3-Y^6-(A^3)_o-Y^7-M^1-Y^8-(A^4)_p-Y^9-Z^4 \qquad II$$

in which the variables have, independently of one another, the following meanings:

$A^3$ and $A^4$
a spacer with a chain length of 1 to 30 C atoms;

$M^1$ a mesogenic group;

$Y^6$ to $Y^9$
a chemical bond, —O—, —S—, —C(=O)—, —C(=O)—O—, —O—C(=O)—, —CH=CH—C(=O)—O—, —O—C(=O)—O—, —C(=O)—N(R$^1$)— or —(R$^1$)N—C(=O)—, —CH$_2$—O—, —O—CH$_2$—, —CH=N—, —N=CH— or —N=N—;

R$^1$ hydrogen, C$_1$–C$_4$-alkyl;

o 0 or 1;

p 0 or 1;

$Z^3$ and $Z^4$
hydrogen, C$_1$–C$_4$-alkyl, a polymerizable group or a radical having a polymerizable group, where at least one of the variables $Z^3$ or $Z^4$ is a polymerizable group or a radical having a polymerizable group, and b$_2$) at least one chiral additive of the formula I with which a cholesteric liquid crystal phase with a pitch of less than 450 nm can be obtained.

In the case of the achiral liquid crystal monomers of the formula II, the same definitions and preferred embodiments apply to the polymerizable groups $Z^3$ and $Z^4$, the bridge members $Y^6$ to $Y^9$, the spacers $A^3$ and $A^4$ and the mesogenic group $M^1$ as to the corresponding variables in formula I.

Just as in formula I, it is also possible to link the mesogenic group directly to the $Z^3$ or $Z^4$ radicals. In these cases, o and/or p are 0 and $Y^6$ and $Y^7$ and/or $Y^8$ and $Y^9$ together are a chemical bond.

The mixture b) additionally contains as chiral additive b$_2$) at least one compound of the formula I described above.

Suitable dopants should have a high twisting ability so that small amounts of the dopant are sufficient to induce the helical structure. In addition, the compatibility of the chiral dopants with the liquid crystal compounds should be good in order to make an efficient interaction between these components possible.

The extent of the twisting depends in each case on the twisting ability of the chiral dopant and on its concentration. This therefore means that the pitch of the helix and in turn also the interference wavelengths depend on the concentration of the chiral dopant. It is therefore impossible to state a generally valid concentration range for the dopant. The dopant is added in the amount which achieves the required UV reflection.

Preferred chiral additives for b$_2$) are compounds of the formula Ia

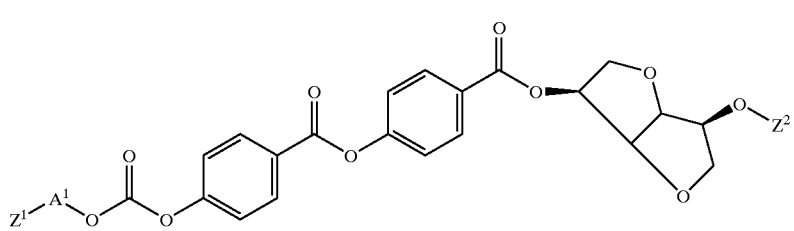

in which the variables have, independently of one another, the following meanings:

$A^1$
 a spacer with a chain length of 1 to 6 C atoms;

$Z^1$ and $Z^2$
 a polymerizable group or a radical having a polymerizable group, where the definition of the variables $A^1$ and $Z^1$ and $Z^2$ corresponds in the general and preferred embodiment to the explanation given above.

Particularly preferred monomers II are those of the following structures:

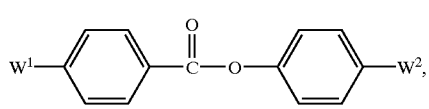

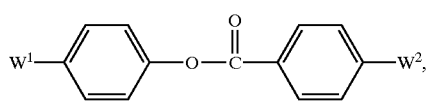

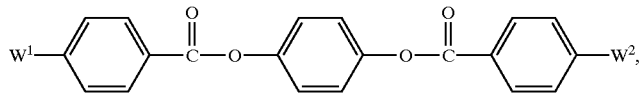

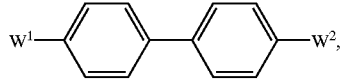

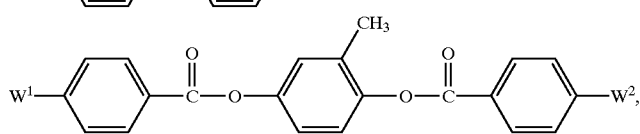

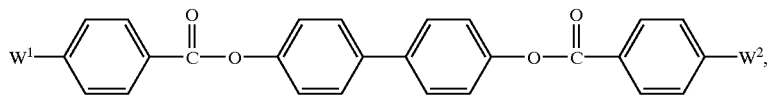

$W^1$: $CH_2=CH-C(=O)-O-(CH_2)_4-O-$, $W^2$: $-O-(CH_2)_4-O-C(=O)-CH=CH_2$

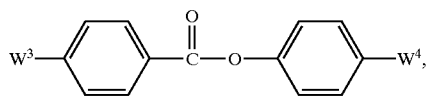

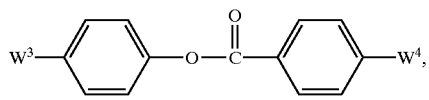

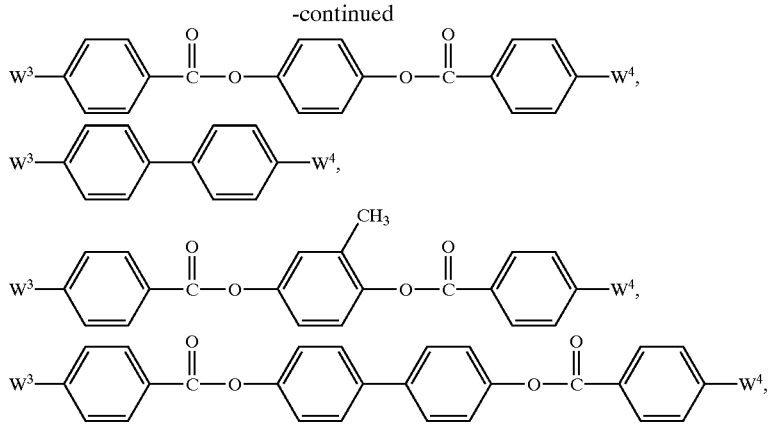
W³: CH₂=CH—C(=O)—O—(CH₂)₆—O—,
W⁴: —O—(CH₂)₆—O—C(=O)—CH=CH₂
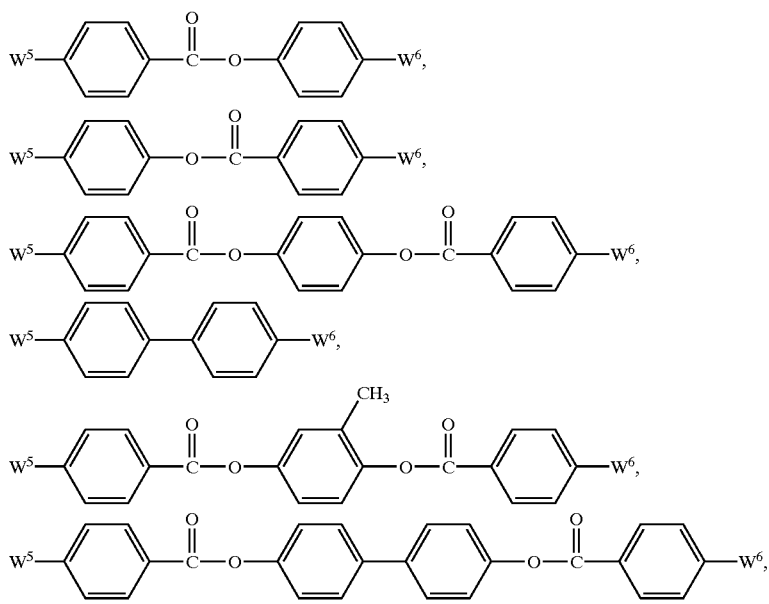
W⁵: CH₂=C(CH₃)—C(=O)—O—(CH₂)₄—O—,
W⁶: —O—(CH₂)₄—O—C(=O)—C(CH₃)=CH₂
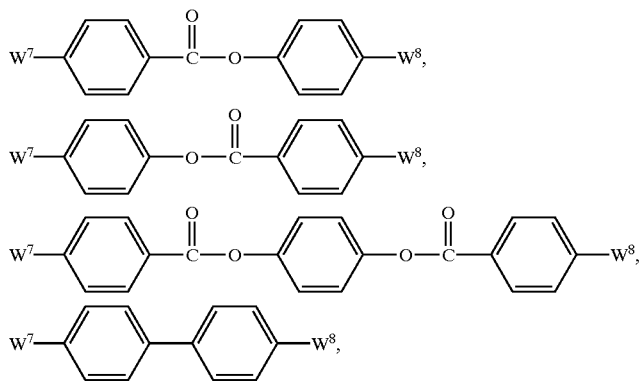

-continued
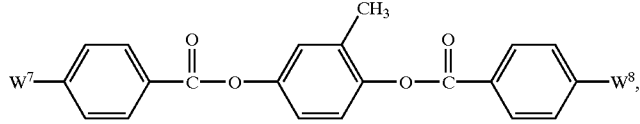
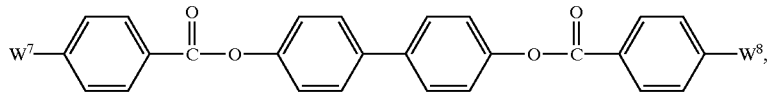
W⁷: $CH_2=C(CH_3)-C(=O)-O-(CH_2)_6-O-$,
W⁸: $-O-(CH_2)_6-O-C(=O)-C(CH_3)=CH_2$
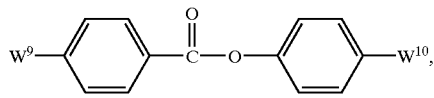
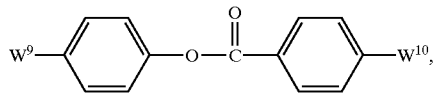
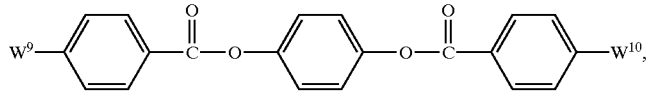
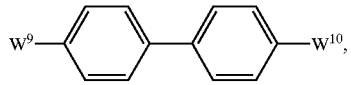
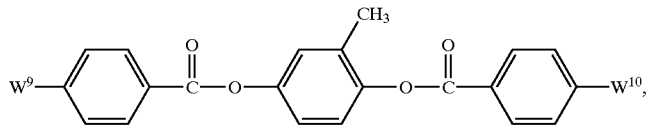
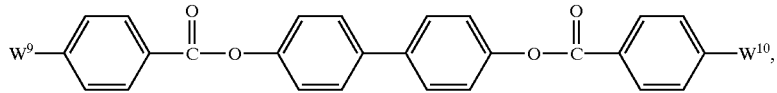
W⁹: $CH_2=CH-C(=O)-O-(CH_2)_4-O-C(=O)-O-$,
W¹⁰: $-O-(O=)C-O-(CH_2)_4-O-C(=O)-CH=CH_2$
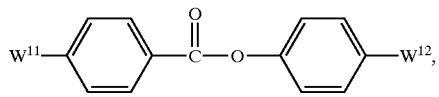 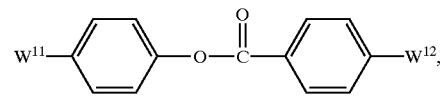
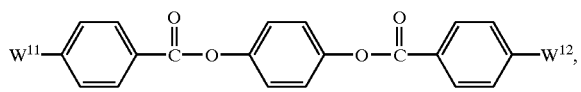 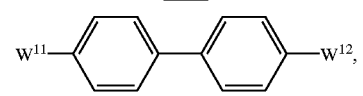
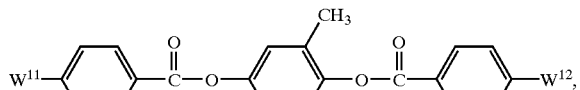
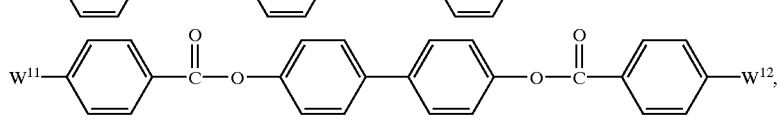
W¹¹: $CH_2=CH-C(=O)-O-(CH_2)_6-O-C(=O)-O-$,
W¹²: $-O-(O=)C-O-(CH_2)_6-O-C(=O)-CH=CH_2$

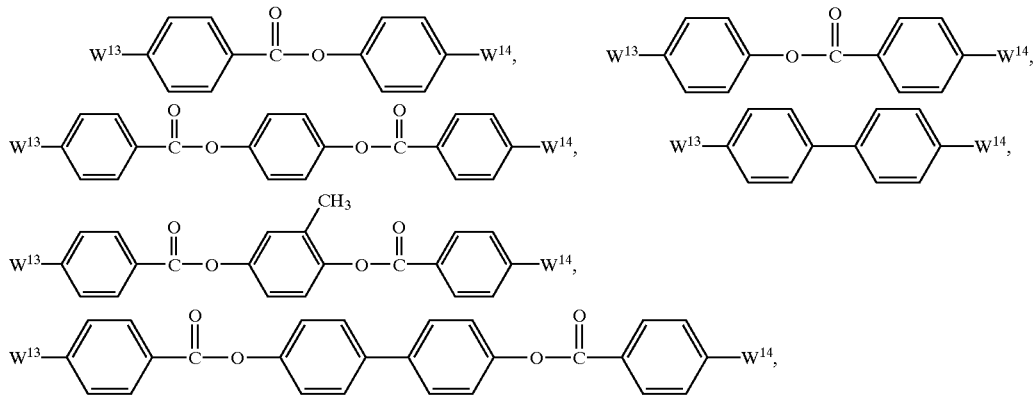
W[13]: $CH_2=C(CH_3)-C(=O)-O-(CH_2)_4-O-C(=O)-O-$
W[14]: $-O-(O=)C-O-(CH_2)_4-O-C(=O)-C(CH_3)=CH_2$
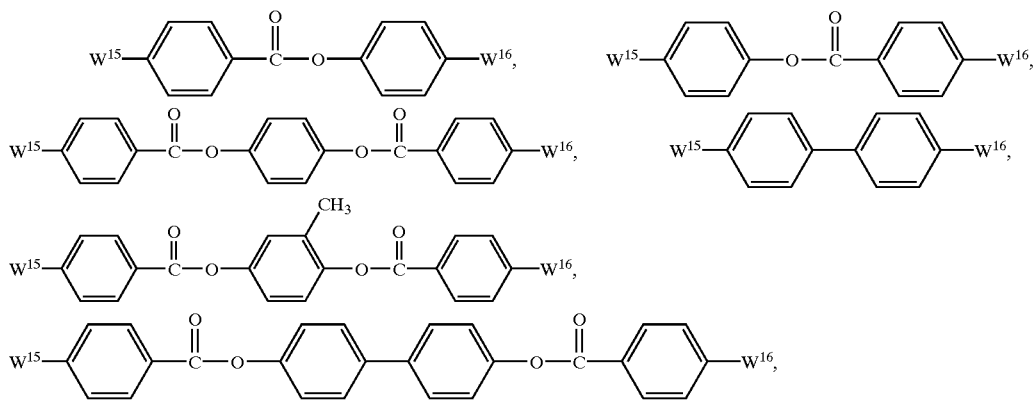
W[15]: $CH_2=C(CH_3)-C(=O)-O-(CH_2)_6-O-C(=O)-O-$,
W[16]: $-O-(O=)C-O-(CH_2)_6-O-C(=O)-C(CH_3)=CH_2$
Particularly preferred monomers I are the following structures containing dianhydromannitol as central building block:
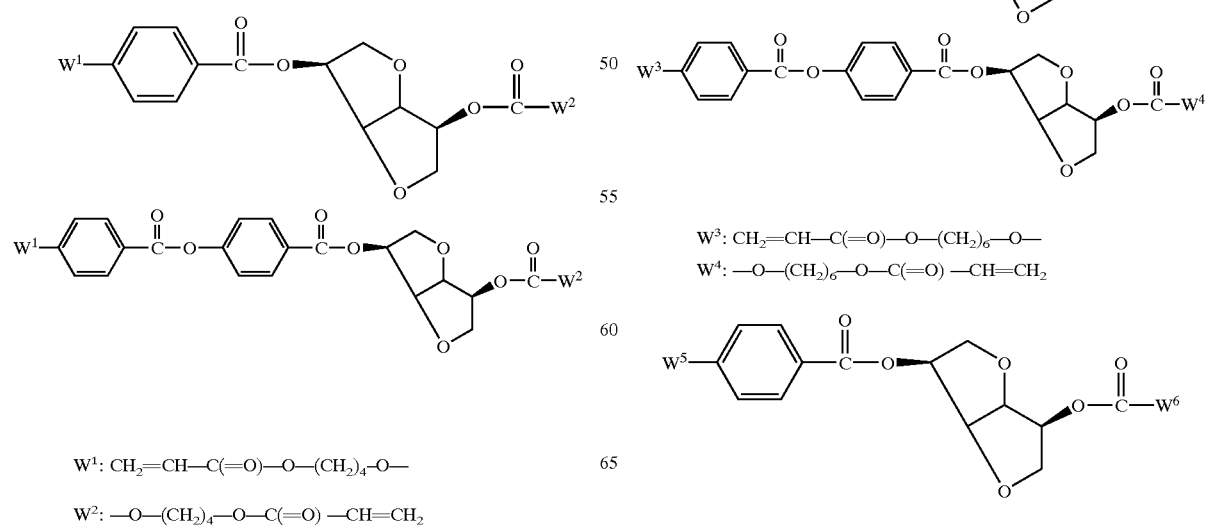
W[1]: $CH_2=CH-C(=O)-O-(CH_2)_4-O-$
W[2]: $-O-(CH_2)_4-O-C(=O)-CH=CH_2$
W[3]: $CH_2=CH-C(=O)-O-(CH_2)_6-O-$
W[4]: $-O-(CH_2)_6-O-C(=O)-CH=CH_2$

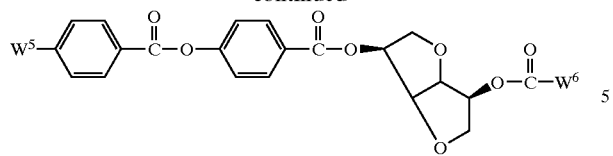

W⁵: $CH_2=C(CH_3)-C(=O)-O-(CH_2)_4-O-$,

W⁶: $-O-(CH_2)_4-O-C(=O)-C(CH_3)=CH_2$

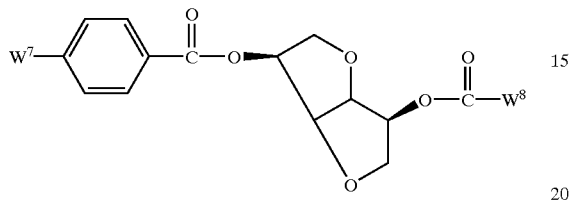

W⁷: $CH_2=C(CH_3)-C(=O)-O-(CH_2)_6-O-$,

W⁸: $-O-(CH_2)_6-O-C(=O)-C(CH_3)=CH_2$

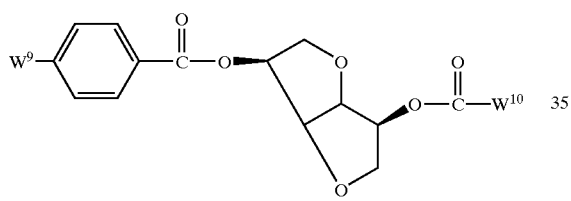

W⁹: $CH_2=CH-C(=O)-O-(CH_2)_4-O-C(=O)-O-$

W¹⁰: $-O-(O=)C-O-(CH_2)_4-O-C(=O)-CH=CH_2$

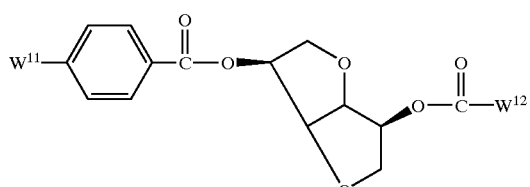

W¹¹: $CH_2=CH-C(=O)-O-(CH_2)_6-O-C(=O)-O-$

W¹²: $-O-(O=)C-O-(CH_2)_6-O-C(=O)-CH=CH_2$

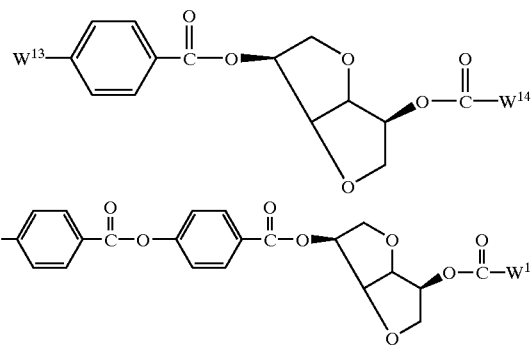

W¹³: $CH_2=C(CH_3)-C(=O)-O-(CH_2)_4-O-C(=O)-O-$,

W¹⁴: $-O-(O=)C-O-(CH_2)_4-O-C(=O)-C(CH_3)=CH_2$

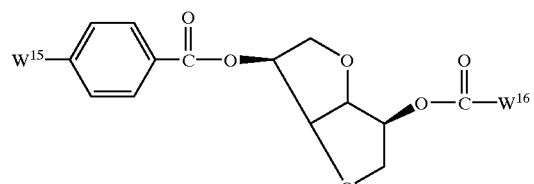

W¹⁵: $CH_2C\ C(CH_3)-C(=O)-O-(CH_2)_6-O-C(=O)-O-$,

W¹⁶: $-O-(O=)C-O-(CH_2)_6-O-C(=O)-C(CH_3)=CH_2$

The ratios by weight of component II to component I are in the range from 99:1 to 40:60, preferably in the range from 99:1 to 70:30, particularly preferably from 98:2 to 85:15.

Use of the cholesteric liquid crystal compositions according to the invention in cosmetic and pharmaceutical preparations:

The photoprotective agents employed in cosmetic and pharmaceutical preparations have the task of preventing or at least reducing the harmful effects of sunlight on human skin. In addition, however, these photoprotective agents serve to protect further ingredients from decomposition or degradation by UV radiation. The intention in hair cosmetic formulations is to reduce damage to keratin fibers by UV rays.

The sunlight reaching the earth's surface contains UV-B rays (280 to 320 nm) and UV-A rays (>320 nm), which follow directly after visible light regions. The effect on the human skin is manifested, especially in the case of UV-B rays, by sunburn. Accordingly, the industry provides a relatively large number of substances which absorb UV-B rays and thus prevent sunburn.

Dermatological studies have shown that UV-A rays are also perfectly able to cause skin damage and allergies by, for example, damaging the keratin or elastin. This reduces the elasticity and water storage capacity of the skin, i.e. the skin becomes less supple and is prone to wrinkling. The noticeably high incidence of skin cancers in areas of strong insolation shows that it is evident that damage to the genetic information in the cell is caused by sunlight, specifically by UV-A rays. All these findings therefore make it appear necessary for efficient filter substances for the UV-A and UV-B regions to be developed.

Besides known UV absorbers such as 2-ethylhexyl 4-methoxycinnamate or 3-(4'-methylbenzylidene)bornan-2-one, frequent use is made in cosmetic and pharmaceutical formulations also of photoprotective agents which, in the form of pigments, reflect or absorb UV rays. The most important of these pigments which are used are titanium dioxide and zinc oxide. It is possible on use at high concentrations to achieve complete covering of the skin with pigments. However, the particles then reflect not only UV rays but also visible light, which results in the frequently unwanted strong intrinsic color of pigment-containing products.

Whereas large-particle titanium dioxide pigments (particle size >500 nm) have comparable effects in the UV-B and UV-A regions, with fine-particle material there is a shift in the spectrum of action in the direction of UV-B with decreasing particle size. This shows that the absorption/reflection characteristics depend directly on the size and the distribution of the particles. Particular particle size distributions are therefore necessary for a balanced protection from UV-B and UV-A.

It proves to be a disadvantage on use of the abovementioned pigments that agglomeration, aggregation and/or separation of the pigment particles frequently occur during storage of the cosmetic or pharmaceutical photoprotective formulations. The consequence of the change in optical properties due to this may be a drastically reduced photoprotective action.

As an alternative to the abovementioned pigments, DE-A-196 19 460 describes the use of liquid crystal mixtures with cholesteric phase comprising a) liquid crystal organosiloxanes which have dianhydrohexitol derivatives as chiral groups, and b) chiral monomeric additives which induce the same helicity as the particular liquid crystal organosiloxanes, for producing UV protective layers which are suitable for cosmetic purposes and are in the form of films or platelets. The liquid crystal mixtures described therein have the disadvantage that they can be processed to pigments only unsatisfactorily because of their high viscosity.

DE-A-196 29 761 describes cosmetic or pharmaceutical preparations containing pigments of polyorganosiloxanes with a color which depends on the angle of view. The pigments in this case comprise at least one oriented crosslinked substance with a liquid crystal structure with chiral phase. It is true that the pigments disclosed therein in the cosmetic and pharmaceutical formulas have certain absorption properties in the UV region. However, they have the disadvantage for particular applications that the compounds in this case are colored, which limits the range of use thereof. Very often, however, it is precisely those cosmetic and pharmaceutical preparations which achieve UV protection but for which it is undesirable for a preparation to be colored which are in demand.

The invention thus also relates to the use of the abovementioned cholesteric liquid crystal compositions as UV filters in cosmetic and pharmaceutical preparations for protecting the human skin or human hair from the sun's rays, alone or together with compounds which absorb in the UV region and are known per se for cosmetic and pharmaceutical preparations.

The cholesteric liquid crystal compositions preferably used as UV filters in cosmetic and pharmaceutical preparations comprise a mixture of at least one achiral liquid crystal polymerizable monomer of the formula II and at least one chiral polymerizable monomer of the formula I.

For the use according to the invention of the abovementioned cholesteric liquid crystal compositions a) and b) as UV filters in cosmetic and pharmaceutical preparations it is possible for the components of the formulae I and II present in these compositions to be incorporated directly into the cosmetic and pharmaceutical preparations.

However, the cholesteric liquid crystal compositions used according to the invention are preferably employed in the form of pigments. These pigments are obtainable by converting the monomers I and II present in the cholesteric liquid crystal compositions by means of their polymerizable groups, by free-radical or ionic polymerization processes which can be started by a photochemical reaction, into highly crosslinked polymers with a frozen liquid crystal order.

The preparation of such pigments is known and is described in detail inter alia in German Application P 19738369.6.

A review of processes for the photochemical crosslinking of oriented starting materials is moreover to be found in C. G. Roffey, Photopolymerisation of Surface Coatings, (1982) John Wiley & Sons, Chichester, pp. 137 to 208.

In a preferred embodiment, the three-dimensionally crosslinkable polymerizable monomers are applied to a substrate, are crosslinked on this substrate and, after the crosslinking, are detached from the substrate.

The cholesteric liquid crystal compositions which have been crosslinked to a film can be comminuted to the particle size required in each case by grinding after the polymerization. Depending on their required application or depending on the nature of the cosmetic or pharmaceutical formulation, it is possible to produce particle sizes with a diameter of from 1 to 1000 $\mu$m. Preferred particle sizes are in the range between 1 and 100 $\mu$m, particularly preferably between 15 and 50 $\mu$m.

The thickness of the pigments is between 1 and 100 $\mu$m, preferably between 1 and 50 $\mu$m, particularly preferably between 1.5 and 10 $\mu$m.

The cholesteric liquid crystal compositions a) and b) suitable as starting materials for producing the pigments have a twisted structure with a pitch corresponding to a wavelength of light up to 450 nm. As shown in the preferred embodiment b), these twisted structures with a defined pitch can be obtained from nematic structures $b_1$) by adding a chiral substance $b_2$). The nature and content of the chiral substance determine the pitch of the twisted structure and thus the wavelength of the reflected light. Depending on the chirality of the optically active additives employed, the twisting of the structure can be either left- or right-handed.

So-called broad-band reflectors can be produced by simply mixing a plurality of the cholesteric liquid crystal pigments to be used according to the invention, each having different UV reflection maxima.

It is moreover possible by mixing at least two different pigments of the cholesteric liquid crystal compositions a) and/or b) with respectively opposite twisting (helicity) to achieve complete reflection of UV rays. Pigments of such cholesteric liquid crystal structures with respectively opposite twisting can be obtained, for example, by adding in each case the individual mirror-image isomers (enantiomers) or diastereomers of the chiral additives $b_2$) to the achiral liquid crystal polymerizable monomer $b_1$). It is moreover possible for the structures with respectively opposite twisting to be identical or different in pitch.

It is also possible first to mix the cholesteric liquid crystal compositions a) or b) with respectively opposite twisting, and then to convert the latter by the abovementioned crosslinking into the pigments described previously and to employ them as UV reflectors in cosmetic and pharmaceutical formulations.

Besides the abovementioned mixtures of cholesteric liquid crystal pigments, it is also possible to produce multilayer pigments whose individual layers comprise different three-dimensionally crosslinked cholesteric liquid crystal compositions to be used according to the invention. The design of such multilayer pigments can be varied in diverse ways. Thus, it is possible inter alia to apply individual layers of crosslinked cholesteric liquid crystal compositions with opposite twisting or individual layers of crosslinked cholesteric liquid crystal compositions with the same helical handedness but different pitch and thus different reflection properties one on top of the other.

Preference is given to three-layer pigments in which the two outer layers each consist of at least one of the crosslinked cholesteric liquid crystal compositions to be used according to the invention, and the middle layer may contain, for example, a binder matrix in which a further UV absorber can additionally be incorporated. Details of the production, properties and other constituents of such multilayer cholesteric pigments are to be found in German Patent Application P 19738368.8.

The invention thus also relates to the pigments described above, in particular multilayer pigments, comprising the cholesteric liquid crystal compositions mentioned at the outset.

One advantage of the pigments used according to the invention is that their composition can be adjusted to make it possible to achieve the required UV reflection with these pigments but without them being intrinsically colored (in the visible region).

The pigments show another advantage in their physical properties. Because of their low density (compared with $TiO_2$ for example), the pigments can be incorporated satisfactorily into emulsions without aggregation or separation of the pigment particles occurring.

The pigments to be used according to the invention can be incorporated into the cosmetic and pharmaceutical preparations simply by mixing.

The present invention further relates to cosmetic and pharmaceutical preparations which comprise 0.1 to 20% by weight, preferably 0.5 to 10% by weight, particularly preferably 1 to 7% by weight, based on the total amount of the cosmetic and pharmaceutical preparation, of one or more of the cholesteric liquid crystal compositions of a) at least one chiral liquid crystal polymerizable monomer of the formula I

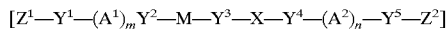

$$[Z^1-Y^1-(A^1)_m-Y^2-M-Y^3-X-Y^4-(A^2)_n-Y^5-Z^2]$$

with which it is possible to obtain a cholesteric liquid crystal phase with a pitch of less than 450 nm, or b) a mixture of at least one achiral liquid crystal polymerizable monomer of the formula II

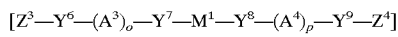

$$[Z^3-Y^6-(A^3)_o-Y^7-M^1-Y^8-(A^4)_p-Y^9-Z^4]$$

and at least one chiral liquid crystal polymerizable monomer of the formula I with which it is possible to obtain a cholesteric liquid crystal phase with a pitch of less than 450 nm, together with compounds which absorb in the UV-A and UV-B regions and are known per se for cosmetic and pharmaceutical preparations, as photoprotective agents. The variables in the formulae. I and II, and the substance class of the chiral additives employed in this case correspond both in their general and in their preferred embodiment to the explanations given above.

Preferred cosmetic and pharmaceutical preparations of those mentioned above are ones which comprise the cholesteric liquid crystal compositions to be used according to the invention in the form of the pigments described above, in particular in the form of multilayer pigments.

The cosmetic and pharmaceutical preparations comprising photoprotective agents are usually based on a vehicle which comprises at least one oil phase. However, preparations solely on an aqueous basis are also possible on use of compounds with hydrophilic substituents. Accordingly, oils, oil-in-water and water-in-oil emulsions, creams and pastes, protective lipstick bases or nongreasy gels are suitable.

Such sunscreen products may accordingly be in liquid, pasty or solid form, for example as water-in-oil creams, oil-in-water creams and lotions, aerosol foam creams, gels, oils, grease sticks, dusting powders, sprays or hydroalcoholic lotions.

Examples of oil components customary in cosmetics are liquid paraffin, glyceryl stearate, isopropyl myristate, diisopropyl adipate, stearyl 2-ethylhexanoate, hydrogenated polyisobutene, petrolatum, caprylic/capric acid triglycerides, microcrystalline wax, lanolin and stearic acid.

Examples of conventional cosmetic auxiliaries which are suitable as additives are coemulsifiers, fats and waxes, stabilizers, thickeners, biogenic active substances, film formers, fragrances, dyes, pearlescent agents, preservatives, pigments, electrolytes (e.g. magnesium sulfate) and pH regulators. Suitable and preferred coemulsifiers are known W/O and O/W emulsifiers such as polyglycerol esters, sorbitan esters or partly esterified glycerides. Typical examples of fats are glycerides; waxes which may be mentioned are, inter alia, beeswax, paraffin wax or microwaxes, where appropriate combined with hydrophilic waxes. Stabilizers which can be employed are metal salts of fatty acids such as magnesium, aluminum and/or zinc stearate. Examples of suitable thickeners are crosslinked polyacrylic acids and their derivatives, polysaccharides, in particular xanthan gum, guar-guar, agar-agar, alginates and tyloses, carboxymethylcellulose and hydroxyethylcellulose, also fatty alcohols, monoglycerides and fatty acids, polyacrylates, polyvinyl alcohol and polyvinylpyrrolidone. Biogenic active substances mean, for example, plant extracts, protein hydrolysates and vitamin complexes. Examples of film formers which can be used are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives, and similar compounds. Examples of suitable preservatives are formaldehyde solution, p-hydroxybenzoate or sorbic acid. Examples of suitable pearlescent agents are glycol distearic esters such as ethylene glycol distearate, but also fatty acids and fatty acid monoglycol esters. Dyes which can be used are the substances suitable and approved for cosmetic purposes, such as those compiled, for example, in the publication "Kosmetische Färbemittel" of the Farbstoffkommission der Deutschen Forschungsgemeinschaft, published in Verlag Chemie, Weinheim, 1984. These dyes are normally employed in a concentration of from 0.001 to 0.1% of the total weight of the mixture.

The preparations according to the invention advantageously comprise one or more antioxidants. Beneficial antioxidants which, however, are to be used optionally may be all natural, synthetic and/or semisynthetic antioxidants suitable or used for cosmetic and/or dermatological applications.

The antioxidants are particularly advantageously selected from the group consisting of:

amino acids (e.g. glycine, histidine, tyrosine, tryptophan) and derivatives thereof, imidazoles (e.g. urocanic acid) and their derivatives, peptides such as D,L-carnosine, D-carnosine, L-carnosine and their derivatives (e.g. anserine), carotenoids (e.g. β-carotene, lycopene) and their derivatives, lipoic acid and derivatives (e.g. dihydrolipoic acid), aurothioglucose, propylthiouracil and other thio compounds (e.g. thioredoxin, glutathione, cysteine, cystine, cystamine and their glycosyl, N-acetyl, methyl, ethyl, propyl, amyl, butyl and lauryl, palmityl, oleyl, γ-linolyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulfoximine compounds (e.g. buthionine sulfoximine, homocysteine sulfoximine, buthionine sulfones, penta-, hexa- and heptathionine sulfoximine) in very low tolerated doses (e.g. pmol to μmol/kg), also (metal) chelators (e.g. α-hydroxy fatty acids, palmitic acid, phytic acid, lactoferrin), α-hydroxy acids (e.g. citric acid, lactic acid, malic acid), humic acid, bile acids, bile extracts, bilirubin, biliverdin, EDTA, EGTA and their derivatives, unsaturated fatty acids and their derivatives (e.g. γ-linolenic acid, linoleic acid, oleic acid), folic acid and its derivatives (e.g. 5-methyltetrahydrofolic acid), ubiquinone and ubiquinol and their derivatives, vitamin C and its derivatives (e.g. ascorbyl palmitate, ascorbyl phosphates, ascorbyl acetates), tocopherols and derivatives (e.g. tocopheryl acetate, tocotrienol), vitamin A and derivatives (e.g. vitamin A palmitate), rutinic acid and its derivatives, ferulic acid and its derivatives, butylated hydroxytoluene, butylated hydroxyanisole, nordihydroguajaretic acid, trihydroxybutyrophenone, uric acid and its derivatives, stilbenes and their derivatives.

The total content of auxiliaries and additives can be 1 to 80, preferably 6 to 40, % by weight, and the nonaqueous content ("active substance") can be 20 to 80, preferably 30 to 70, % by weight based on the preparation. The preparation can be produced in a manner known per se, i.e. for example by hot, cold, hot/cold or PIT emulsification. These are purely mechanical processes, no chemical reaction taking place.

Finally, it is possible for other substances absorbing in the UV region also to be present as long as they are stable in the complete system of the combination of UV filters to be used according the invention.

Most of the photoprotective agents in the cosmetic and pharmaceutical preparations used to protect the human epidermis consist of compounds which absorb UV light in the UV-B region, i.e. in the region from 280 to 320 nm. For example, the content of the cholesteric liquid crystal compositions to be used according to the invention is 10 to 90% by weight, preferably 20 to 70% by weight, based on the total amount of UV-B and UV-A absorbing substances.

Any UV-A and UV-B filter substances are suitable as UV filter substances to be used in combination with the cholesteric liquid crystal compositions to be used according to the invention.

Examples which may be mentioned are:

| No. | Substance | CAS No. (= acid) |
|---|---|---|
| 1 | 4-aminobenzoic acid | 150-13-0 |
| 2 | 3-(4'-trimethylammoniobenzylidene)bornan-2-one methyl sulfate | 52793-97-2 |
| 3 | 3,3,5-trimethylcyclohexyl salicylate (homosalate) | 118-56-9 |
| 4 | 2-hydroxy-4-methoxybenzophenone (oxybenzonum) | 131-57-7 |
| 5 | 2-phenylbenzimidazole-5-sulfonic acid and its potassium, sodium and triethanolamine salts | 27503-81-7 |
| 6 | 3,3'-(1,4-phenylenedimethine)bis(7,7-dimethyl-2-oxobicyclo[2.2.1]heptane-1-methanesulfonic acid) and its salts | 90457-82-2 |
| 7 | polyethoxyethyl 4-bis(polyethoxy)amino-benzoate | 113010-52-9 |
| 8 | 2-ethylhexyl 4-dimethylaminobenzoate | 21245-02-3 |
| 9 | 2-ethylhexyl salicylate | 118-60-5 |
| 10 | isoamyl 4-methoxycinnamate | 71617-10-2 |
| 11 | 2-ethylhexyl 4-methoxycinnamate | 5466-77-3 |
| 12 | 2-hydroxy-4-methoxybenzophenone-5-sulfonic acid (sulisobenzonum) and the sodium salt | 4065-45-6 |
| 13 | 3-(4'-methylbenzylidene)bornan-2-one | 36861-47-9 |
| 14 | 3-benzylidenebornan-2-one | 15087-24-8 |
| 15 | 1-(4'-isopropylphenyl)-3-phenylpropane-1,3-dione | 63250-25-9 |
| 16 | 4-isopropylbenzyl salicylate | 94134-93-7 |
| 17 | 2,4,6-tri(p-2-ethylhexoxycarbonylanilino)-1,3,5-triazine | 88122-99-0 |
| 18 | 3-(4-imidazolyl)acrylic acid and its ethyl ester | 104-98-3 |
| 19 | ethyl 2-cyano-3,3-diphenylacrylate | 5232-99-5 |
| 20 | 2'-ethylhexyl 2-cyano-3,3-diphenylacrylate | 6197-30-4 |
| 21 | menthyl o-aminobenzoate or: 5-methyl-2-(1-methylethyl)cyclohexyl-2-aminobenzoate | 134-09-8 |
| 22 | glyceryl p-aminobenzoate or: 4-aminobenzoic acid 1-glyceryl ester | 136-44-7 |
| 23 | 2,2'-dihydroxy-4-methoxybenzophenone (dioxybenzone) | 131-53-3 |
| 24 | 2-hydroxy-4-methoxy-4-methylbenzophenone (mexenone) | 1641-17-4 |
| 25 | triethanolamine salicylate | 2174-16-5 |
| 26 | dimethoxyphenylglyoxylic acid or: sodium 3,4-dimethoxyphenylglyoxylate | 4732-70-1 |
| 27 | 3-(4'-sulfobenzylidene)bornan-2-one and its salts | 56039-58-8 |
| 28 | 4-tert-butyl-4'-methoxydibenzoylmethane | 70356-09-1 |
| 29 | 2,2',4,4'-tetrahydroxybenzophenone | 131-55-5 |

Finally, mention may also be made of micronized pigments such as titanium dioxide and zinc oxide.

T protect human hair from UV rays, the cholesteric liquid crystal compositions a) ad/or b) used according to the invention can be incorporated into shampoos, lotions, gels, hair sprays, aerosol foam creams or emulsions in concentrations of 0.1 to 20% by weight, preferably 0.5 to 10% by weight, particularly preferably 1 to 7% by weight. The particular formulations can be used inter alia for washing, coloring and setting the hair.

The compositions to be used according to the invention usually have a particularly high reflectance in the region of the UV-A and UV-B rays with a sharp band structure. They are in addition easily incorporated into cosmetic and pharmaceutical formulations. In particular, moreover, they have high photostability and the preparations produced therewith have a pleasant skin feel.

The UV filter action of the cholesteric liquid crystal compositions a) and/or b) used according to the invention can also be utilized for stabilizing active substances and auxiliaries in cosmetic and pharmaceutical formulations.

DETAILED DESCRIPTION OF THE INVENTION

The following examples are intended to explain in detail the use according to the invention of the cholesteric liquid crystal compositions.

EXAMPLE 1

Preparation of the Chiral Dopant of the Formula Ib

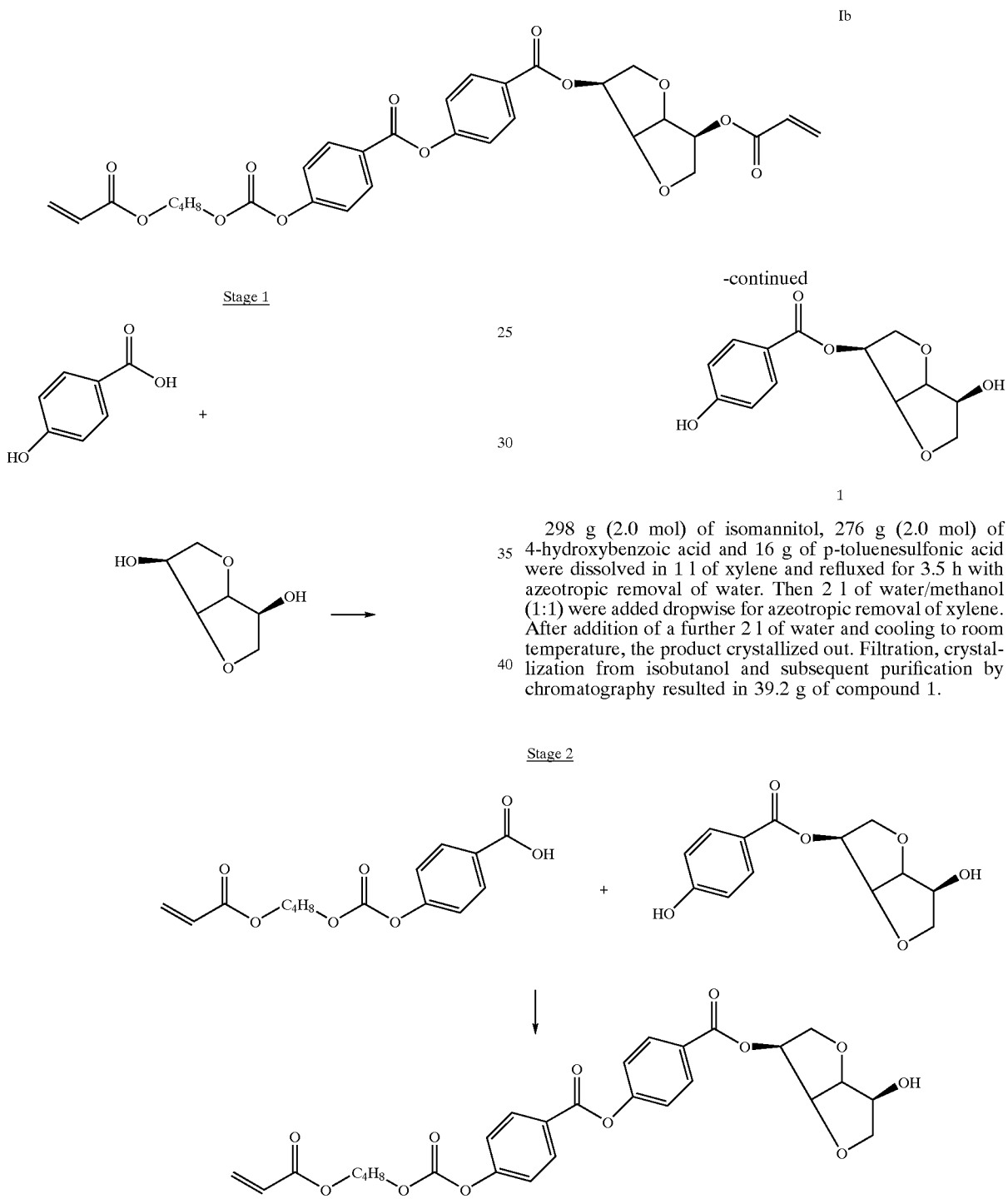

298 g (2.0 mol) of isomannitol, 276 g (2.0 mol) of 4-hydroxybenzoic acid and 16 g of p-toluenesulfonic acid were dissolved in 1 l of xylene and refluxed for 3.5 h with azeotropic removal of water. Then 2 l of water/methanol (1:1) were added dropwise for azeotropic removal of xylene. After addition of a further 2 l of water and cooling to room temperature, the product crystallized out. Filtration, crystallization from isobutanol and subsequent purification by chromatography resulted in 39.2 g of compound 1.

At 0 to 5° C., 0.1 g of 4-dimethylaminopyridine and, in stages over 1 h, 24.72 g of dicyclohexylcarbodiimide were added to a mixture of 28.2 g (0.106 mol) of monoacylated isomannitol of the formula I, prepared in stage 1, and 36.96 g (0.12 mol) of 4-acryloxybutyloxycarbonyloxybenzoic acid in 150 ml of dichloromethane. The reaction mixture was stirred at 0 to 5° C. for 2.5 h and at RT for 12 h and filtered with suction, and the concentrated filtrate was purified by chromatography on silica gel. 45.9 g of compound 2 were obtained.

Stage 3

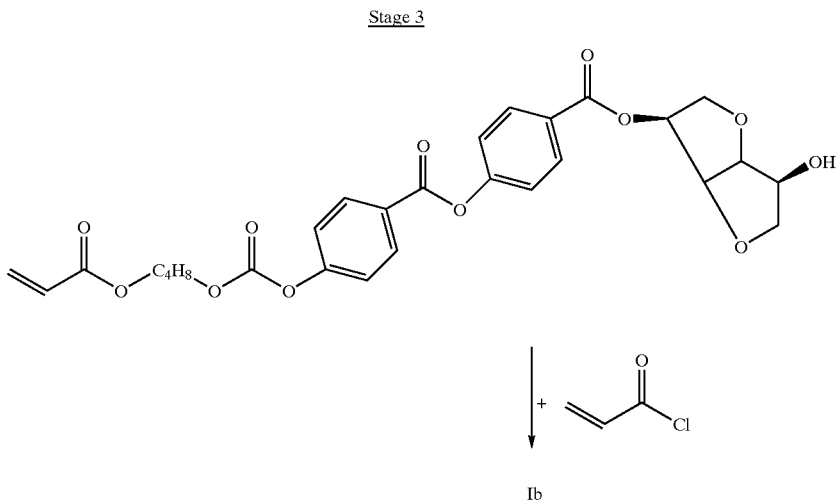

Ib 34.89 g (0.066 mol) of the product from stage 2 were dissolved in 120 ml of dichloromethane together with 27.7 ml (0.2 mol) of triethylamine and, at 0 to 5° C., 9.53 ml (0.12 mol) of acryloyl chloride dissolved in 50 ml of dichloromethane were added. After stirring at 0 to 5° C. for 2 h and at RT for 12 h, the reaction mixture was poured into dilute hydrochloric acid, and the organic phase was washed with water. After the organic phase had been dried over sodium sulfate, the solution was inhibited with Uvinul® FK 4245 (from BASF AG), and the product was purified by chromatography on silica gel. 18.4 g of compound Ib were obtained.

We claim:

1. A chiral dopant of the formula I

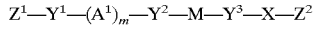   I in which the variables have, independently of one another, the following meanings:

$A^1$
    a spacer with a chain length of 1 to 30 C atoms;
$Y^1$ to $Y^3$
    a chemical bond, —O—, —S—, —C(=O)—, —C(=O)—O—, —O—C(=O)—, —CH=CH—C(=O)—O—, —O—C(=O)—O—, —C(=O)—N(R)— or (R)N—C(=O)—, —CH2—O—, —O—CH2—, —CH=N— or —N=CH— or —N=N—;
M a mesogenic group;
R hydrogen, $C_1$–$C_4$-alkyl;
$Z^1$
    hydrogen, $C_1$–$C_4$-alkyl, a polymerizable group or a radical having a polymerizable group;
$Z^2$ $C_1$–$C_4$-alkyl, a polymerizable group or a radical having a polymerizable group;
X a dianhydrohexitol residue selected from the group consisting of dianhydrosorbitol, dianhydromannitol and dianhydroiditol;
m 0 or 1;
where the radicals $Z^1$, $Z^2$, $Y^1$ to $Y^3$, can be identical or different, and at least one $Z^1$ or $Z^2$ radical is a polymerizable group or a radical comprising a polymerizable group.

2. A chiral dopant as claimed in claim 1, in which the variables have, independently of one another, the following meanings:

$A^1$
    a spacer with a chain length of 1 to 6 C atoms;
$Y^1$ to $Y^3$
    a chemical bond, —O—, —S—, —C(=O)—, —C(=O)—O—, —O—C(=O)—;
M a mesogenic radical from the group consisting of:

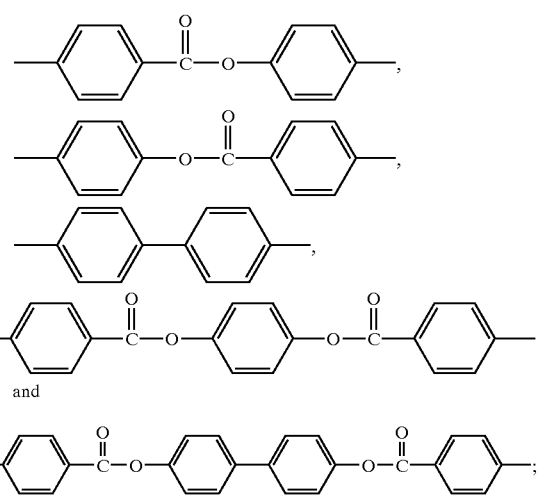

$Z^1$ and $Z^2$
    a polymerizable group or a radical having a polymerizable group;
X a dianhydromannitol residue;
m 0 or 1.

3. A chiral dopant as claimed in claim 1 of the formula Ia,

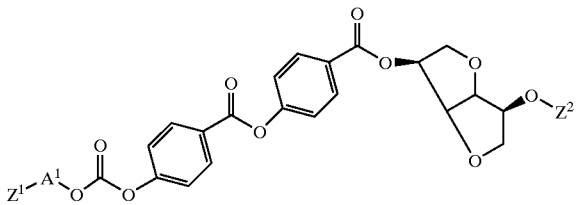

Ia in which the variables have, independently of one another, the following meanings:
$A^1$
 a spacer with a chain length of 1 to 6 C atoms;
$Z^1$ and $Z^2$
a polymerizable group or a radical having a polymerizable group.

4. A cholesteric liquid crystal composition comprising
a) at least one chiral liquid crystal polymerizable monomer of the formula I

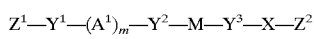

I in which the variables have the meaning stated in claim 1, with which monomer it is possible to obtain a cholesteric liquid crystal phase with a pitch of less than 450 nm
or
b) a mixture of
  $b_1$) at least one achiral liquid crystal polymerizable monomer of the formula II

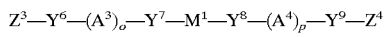

II in which the variables have, independently of one another, the following meanings:
$A^3$ and $A^4$
 a spacer with a chain length of 1 to 30 C atoms;
$M^1$ a mesogenic group;
$Y^6$ to $Y^9$
 a chemical bond, —O—, —S—, —C(=O)—, —C(=O)—O—, —O—C(=O)—, —CH=CH—C(=O)—O—, —O—C(=O)—O—, —C(=O)—N($R^1$)— or —($R^1$)N—C(=O)—, —CH$_2$—O—, —O—CH$_2$—, —CH=N—, —N=CH— or —N=N—;

$R^1$ hydrogen, $C_1$–$C_4$-alkyl;
o 0 or 1;
p 0 or 1;
$Z^3$ and $Z^4$
 hydrogen, $C_1$–$C_4$-alkyl, a polymerizable group or a radical having a polymerizable group,
 where at least one of the variables $Z^2$ or $Z^3$ is a polymerizable group or a radical having a polymerizable group, and
 $b_2$) at least one chiral liquid crystal polymerizable monomer of the formula I with which a cholesteric liquid crystal phase with a pitch of less than 450 nm can be obtained.

5. A cholesteric liquid crystal composition as claimed in claim 4, comprising as chiral liquid crystal polymerizable monomer a) or $b_2$) at least one chiral compound of the formula Ia,

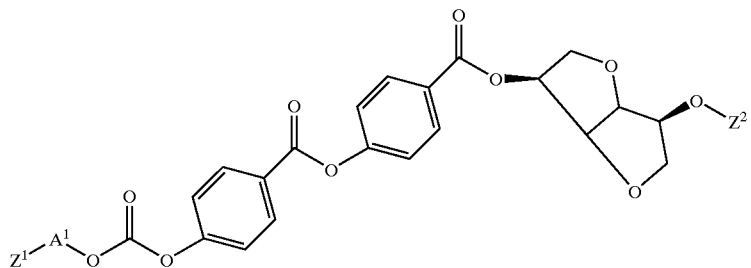

Ia in which the variables have, independently of one another, the following meanings:
$A^1$
 a spacer with a chain length of 1 to 6 C atoms;
$Z^1$ and $Z^2$
a polymerizable group or a radical having a polymerizable group.

6. A cholesteric liquid crystal composition as claimed in claim 4, which reflects left-circularly-polarized light in the UV region.

7. A pigment comprising a polymerized cholesteric liquid crystal composition as defined in claim 4.

8. A pigment as claimed in claim 7, which is a multilayer pigment.

9. A cosmetic or pharmaceutical preparation for protecting the human epidermis or human hair from UV light in the range from 280 to 400 nm, which comprises in a cosmetically or pharmaceutically suitable vehicle, alone or together with compounds which absorb in the UV region and are known per se for cosmetic or pharmaceutical preparations, a cholesteric liquid crystal composition as defined in claim 4 in amounts effective as photostable UV filters.

10. A cosmetic or pharmaceutical preparation as claimed in claim 9, comprising a cholesteric liquid crystal composition in the form of a pigment as UV filter.

11. A cosmetic or pharmaceutical preparation as claimed in claim 9, comprising a cholesteric liquid crystal composition in the form of a multilayer pigment as UV filter.

* * * * *